United States Patent [19]

Fischer et al.

[11] 4,450,300
[45] May 22, 1984

[54] PROCESS FOR THE CONTINUOUS MANUFACTURE OF N-BUTYRALDEHYDE BY SELECTIVE HYDROGENATION OF CROTONALDEHYDE IN THE LIQUID PHASE IN THE PRESENCE OF A PALLADIUM-ALUMINUM OXIDE CATALYST

[75] Inventors: Lothar Fischer; Manfred Z. Hausen; Kurt Wember, all of Marl, Fed. Rep. of Germany

[73] Assignee: Chemische Werke Huels Aktiengesellschaft, Marl, Fed. Rep. of Germany

[21] Appl. No.: 357,451

[22] Filed: Mar. 12, 1982

[30] Foreign Application Priority Data

Dec. 23, 1981 [DE] Fed. Rep. of Germany ....... 3151086

[51] Int. Cl.$^3$ ............................................. C07C 45/62
[52] U.S. Cl. .................................................... 568/462
[58] Field of Search ......................................... 568/462

[56] References Cited

U.S. PATENT DOCUMENTS

| | | | |
|---|---|---|---|
| 2,485,989 | 10/1949 | Smith | 568/462 |
| 2,930,765 | 3/1960 | Cooper et al. | 252/473 |
| 2,930,766 | 3/1960 | Lacey | 252/473 |
| 4,177,214 | 12/1979 | Siclari | 568/462 |

*Primary Examiner*—Werren B. Lone
*Attorney, Agent, or Firm*—Millen & White

[57] ABSTRACT

For the continuous manufacture of n-butyraldehyde by selective hydrogenation of crotonaldehyde, the hydrogenation is conducted in the liquid phase in the presence of a palladium-aluminum oxide supported catalyst containing the palladium in the outer layer of the supporting grain of a thickness of 0.05–0.2 mm. The palladium content of this catalyst is 0.1–0.6% by weight. The aluminum oxide support, with a specific pore volume of 0.4–0.6 cm$^3$/g, has 40–60% of its pores of a diameter of >0.5 nm and an internal surface area of 130–160 m$^2$/g. The hydrogenation is conducted under absolute pressures of 5–50 bar and at temperatures of 20°–100° C. The resultant n-butyraldehyde is of a high purity without interfering by-products.

12 Claims, No Drawings

PROCESS FOR THE CONTINUOUS MANUFACTURE OF N-BUTYRALDEHYDE BY SELECTIVE HYDROGENATION OF CROTONALDEHYDE IN THE LIQUID PHASE IN THE PRESENCE OF A PALLADIUM-ALUMINUM OXIDE CATALYST

BACKGROUND OF THE INVENTION

In the selective catalytic hydrogenation of crotonaldehyde using platinum-metal-type catalysts to obtain n-butyraldehyde, losses of about 5% arise due to the formation of carbon monoxide and propylene. These disadvantages are avoided by the process of DAS [German Published Application] 1,070,160 (=U.S. Pat. No. 2,930,765 and U.S. Pat. No. 2,930,766) by using metal catalysts of the platinum group on supports having a slightly alkaline activity. The selective hydrogenation of crotonaldehyde to n-butyraldehyde in this process takes place in the gaseous phase under normal pressure. However, only unsatisfactory space-time yields are obtained.

Therefore, there is great interest in providing an improved method for the selective hydrogenation of crotonaldehyde with higher space-time yields.

SUMMARY OF THE INVENTION

Accordingly, it is an object of this invention to provide such an improved method.

Upon further study of the specification and appended claims, further objects and advantages of this invention will become apparent to those skilled in the art.

These objects have been achieved by providing a process for the continuous production of n-butyraldehyde by selective hydrogenation of crotonaldehyde, comprising conducting the hydrogenation in the liquid phase in the presence of a palladium-aluminum oxide supported catalyst containing the palladium in the outer layer of the supporting grain of a thickness of 0.05–0.2 mm, the support of this catalyst, with a total specific pore volume of 0.4–0.6 cm$^3$/g, having 40–60% of its pore volume in the form of pores having a diameter of above 7.5 nm with a specific internal surface area of 130–160 m$^2$/g, and the palladium content of this catalyst being 0.1–0.6% by weight, under an absolute pressure of 5–50 bar and at a temperature of 20°–100° C.

DETAILED DISCUSSION

Surprisingly, n-butyraldehyde is selectively obtained in high space-time yields by the hydrogenation of crotonaldehyde in the liquid phase in the presence of a palladium-aluminum oxide supported catalyst prepared in a special way, with an almost quantitative conversion of crotonaldehyde. The formation of gaseous by-products has not been detected.

The n-butyraldehyde obtained in accordance with this invention is, surprisingly, of such a high purity and so free of interfering by-products that it can be continuously conventionally converted into 2-ethylhexenal without distillatory purification; this product can then be hydrogenated in a conventional process to 2-ethylhexanol-1. The yield of 2-ethylhexanol is 96% and thus just as high as from the use of pure n-butyraldehyde prepared by the oxo synthesis. 2-ethylhexanol-1 is useful as plasticizer, leibricants and for the production of other chemical products.

Even though the process of this invention, carried out in the liquid phase, eliminates the vaporization of crotonaldehyde for purifying purposes, no decrease of catalyst activity can be perceived even after its long-term use, for example, after 8 months.

Per this invention, the crotonaldehyde is selectively hydrogenated in the liquid phase under an absolute pressure of 5–50 bar, preferably 10–20 bar and at a temperature of 20°–100° C., preferably 40°–60° C., on a palladium-aluminum oxide supported catalyst. The γ-modification is preferably employed as the aluminum oxide. In the aluminum oxide suitable for the process of this invention, 40–60%, preferably 45–55%, especially 50% of the special pore volume is constituted by pores of a diameter larger than 7.5 nm. The total specific pore volume is 0.4–0.6 cm$^3$/g, preferably 0.45–0.50 cm$^3$g, and the specific internal surface area is 130–160 m$^2$/g, preferably 140–155 m$^2$/g, especially 150 m$^2$/g.

The palladium is deposited in the outer layer of the aluminum oxide functioning as the support. That is, the palladium is present in the perimeter thickness, i.e., outer region of the support. The palladium content ranges around 0.1–0.6%, preferably 0.3–0.5% by weight and the thickness of the outer layer is 0.05–0.2 mm, preferably 0.08–0.15 mm, as required for the reaction according to this invention.

Placement of the palladium in the outer perimeter zone of the support can be accomplished by conventional procedures as disclosed, e.g., in M. G. Howden and T. A. J. Hardenberg, CSIR Report CENG 349 (1980), 1 to 17 and exemplified herein. Where necessary, routine preliminary experiments can be employed to assure that the proper boundary zone thickness has been achieved, e.g., using diagnostic methods such as miseroscopic inspection using a calibrated graticule or energy-dispersitive X-ray microanalysis employed in connection with scanning electron microscopy.

The shape of the catalyst is without effect on the catalytic behavior. However, the particle size is important if the conversion is based on the catalyst bed volume. With increasing particle size, conversion drops; thus, it is generally desirable to choose the particles to be as small as possible. This, in turn, increases the pressure loss. For this reason, a compromise must be found between conversion and pressure loss. The size of the catalyst particles is 1–5 mm, preferably 2–4 mm. For example, rod shaped particles are often preferred and have a diameter of 1–5 mm and a length of 2–10 mm.

Specified amounts of reactants per hour per weight unit of catalyst used can be conventionally determined in accordance with the foregoing discussion and other considerations and the following examples.

In general, the flow rates for crotonaldehyde will be in the range of 0.3–1.0 l/l catalyst.h and for hydrogen will be in the range of 80–270 l/l catalyst.h under normal conditions (STP).

In the process of this invention, space-time yields are 0.8–0.9 l aldehyde/l catalyst.h, as well as yields in n-butyraldehyde of 98–99%, based on crotonaldehyde, with a practically 100% conversion rate. 2-Ethylhexenal is obtained as the by-product, which does not interfere in the subsequent reaction to obtain 2-ethylhexanol. No gaseous by-products have been found.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1a 1.25 kg of γ-aluminum oxide in rod shape particles (diameter: 3.2 mm) having a specific pore volume of 0.45 cm$^3$/g, 45% of its pores having a diameter larger than 7.5 nm and having a specific internal surface area of 153 m$^2$.gm was sprayed, while being turned, in a pelletizing drum at 90°–100° C. with 800 cm$^3$ of an aqueous solution containing 6.3 g of palladium in the form of palladium(II) chloride and 1.1 g of hydrogen chloride. The batch was dried for 15 minutes and calcined in an air stream at 350° C., thus obtaining 1.26 kg of a palladium-aluminum oxide catalyst containing 0.5% by weight of palladium in the outer layer of the supporting grain of a thickness of 0.11±0.04 mm, the catalyst particles having a diameter of 3.2 mm.

EXAMPLE 1b 4.07 kg of γ-aluminum oxide in rod shape particles (diameter: 1.6 mm) having a specific pore volume of 0.44 cm$^3$/g, with 50% of its pores of a diameter larger than 7.5 nm and with a specific internal surface area of 145 m$^2$/g, was sprayed, while being turned, in a pelletizing drum at 95°–105° C. with 2.6 l of an aqueous solution containing 20.5 g of palladium in the form of palladium(II) nitrate and 60 g of HNO$_3$. The batch was dried for 16 hours at 110° C. and finally calcined for 4 hours at 450° C. in an air stream, thus obtaining 3.91 kg of a palladium-aluminum oxide catalyst containing 0.5% by weight of palladium in the outer layer of the supporting grain of 0.10±0.05 mm in thickness, the catalyst particles having a diameter of 1.6 mm.

EXAMPLE 1c 200 cm$^3$ of the catalyst produced according to the process of Example 1a and containing 0.5% palladium, was first treated at 200° C. with hydrogen to reduce the deposited palladium compound to palladium. Thereafter, the catalyst was filled into a reactor and provided with a top layer and a bottom layer of an inert material. The reactor consisted of a jacketed pipe having an internal diameter of 24 mm and a length of 2.60 m. A heat-transfer fluid circulated in the jacket. At this point in time, liquid crotonaldehyde (water content: 9%) and hydrogen were conducted from the top toward the bottom over the catalyst, the throughput of liquid crotonaldehyde being 150 g/h and that of the gaseous hydrogen, calculated under normal conditions (STP), being 48 l/h. The absolute pressure was 16 bar and the temperature was 50° C. A product stream was obtained of 153 g/h, consisting of 94.3% by weight of an organic phase with a water content of 3% by weight and an acid number of 0.4 mg KOH/g and of 5.7% by weight of an aqueous phase, the water content of which amounted to 95% by weight. The anhydrous organic phase consisted of 98.5% by weight of n-butyraldehyde, 0.4% by weight of butanol, 0.1% by weight of crotonaldehyde, and 1.0% by weight of by-products, essentially 2-ethylhexenal.

During a testing time of 5 months, no change in the aforementioned composition of the product stream was observed.

Conversion: 100%
Yield: 98.3%
Space-Time Yield: 0.84 l butyraldehyde/l catalyst.h Utilizing the catalyst obtained according to the process of Example 1b, comparable results were achieved.

EXAMPLE 2a 1.25 kg of γ-aluminum oxide particles in the form of rods (diameter: 1.6 mm) having a specific pore volume of 0.58 cm$^3$/g, 48% of its pores having a diameter which is >7.5 nm and with a specific internal surface area of 160 m$^2$/g, was sprayed, while being turned, in a pelletizing drum at 90°–100° C. with 800 cm$^3$ of an aqueous solution containing 1.25 g of palladium in the form of palladium(II) nitrate and 18 g of HNO$_3$. The batch was dried at 110° C. for 16 hours and thereafter calcined for 4 hours at 450° C. in an air stream. Yield: 1.25 kg of a palladium-aluminum oxide catalyst containaing 0.1% by weight of palladium in the outer layer of the supporting grain having a thickness of 0.1 mm.

EXAMPLE 2b

The hydrogenation of crotonaldehyde with 9% water was conducted according to the details of Example 1c using 200 cm$^3$ of the γ-aluminum oxide-supported catalyst produced according to Example 2a, containing 0.1 palladium, at 90° C. under a hydrogen pressure of 40 bar for the selective production of n-butyraldehyde.

All other details correspond to the data of Example 1c. Conversion remained practically complete over a testing period of 2 months. The yield of n-butyraldehyde, determined by gas chromatography, was 98.6%.

EXAMPLE 3a 1.25 kg of γ-aluminum oxide rod shape particles (diameter: 3.2 mm) having a specific pore volume of 0.50 cm$^3$/g (44% of the pores had a diameter of >7.5 nm) and with a specific internal surface area of 140 m$^2$/g, was sprayed, while being turned, in a pelletizing drum at 90°–100° C. with 800 cm$^3$ of an aqueous solution containing 7.5 g of palladium in the form of palladium(II) nitrate and 18 g of HNO$_3$. The batch was dried and calcined as described in Example 2a, thus obtaining 1.26 kg of a palladium-aluminum oxide catalyst containing 0.6% by weight of palladium in the outer layer of the supporting grain of a thickness of 0.15 mm.

EXAMPLE 3b

According to the description of Example 1c, crotonaldehyde with 9% water was hydrogenated selectively into n-butyraldehyde using 200 cm$^3$ of the palladium-alumina catalyst, containing 0.6% palladium, produced according to Example 3a, at 30° C. and under a hydrogen pressure of 5 bar for 8 months. All other details corresponded to those of Example 1c. With a practically complete conversion during the entire testing period, the yield of n-butyraldehyde was 98.1–98.6%.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the continuous production of n-butyraldehyde by selective hydrogenation of crotonaldehyde, comprising conducting the hydrogenation in the liquid phase in the presence of hydrogen and in the presence of a palladium-aluminum oxide supported catalyst, under an absolute pressure of 5–50 bar and at a temperature of 20°–100° C. with a flow rate under STP conditions for crotonaldehyde in the range of 0.3–1.0 l/l catalyst.h and for hydrogen in the range of 80–270 l/l catalyst.h, and the catalyst having a particle size of 1–5 mm and the palladium being contained therein in the outer thickness of 0.05–0.2 mm of the support, the catalyst having a total specific pore volume of 0.4–0.6 cm$^3$/g, a specific internal surface area of 130–160 m$^2$/g, having 40–60% of its pore volume in the form of pores having a diameter above 7.5 mm, and the palladium content of the catalyst being 0.1–0.6% by weight.

2. A process of claim 1, wherein the aluminum support is γ-aluminum oxide.

3. A process of claim 1 wherein the palladium-aluminum supported catalyst contains 0.3–0.5% by weight of palladium.

4. A process of claim 1 wherein the total specific pore volume of the support is 0.45–0.50 cm$^3$/g.

5. A process of claim 1 wherein 45–55% of the pore volume of the support is constituted by pores of a diameter of >7.5 nm.

6. A process of claim 5 wherein 50% of the pore volume of the support is constituted by pores of a diameter >7.5 nm.

7. A process of claim 1 wherein the pores have a specific internal surface area of 140–155 m$^2$/g.

8. A process of claim 1 wherein the pores have a specific internal surface area of 150 m$^2$/g.

9. A process of claim 1 wherein the temperature is 40°–60° C. and the absolute pressure is 10–20 bar.

10. A process of claim 1 wherein the particle size of the catalyst is 2–4 mm.

11. A process of claim 1 wherein the aluminum support of the catalyst is γ-aluminum oxide of a total specific pore volume of 0.45–0.50 cm$^3$/g, 45–55% of its pores having a diameter >7.5 nm and its pores having an internal surface area of 140–155 m$^2$/g; the catalyst contains 0.3–0.5% of palladium and having a particle size of 2–4 mm; and the reaction is conducted at 40°–60° C. and with an absolute pressure of 10–20 bar.

12. A process of claim 1, wherein the space-time yield is 0.8–0.9 l aldehyde/l catalyst.

* * * * *